(12) United States Patent
Dussarrat et al.

(10) Patent No.: US 9,593,133 B2
(45) Date of Patent: Mar. 14, 2017

(54) ORGANOSILANE PRECURSORS FOR ALD/CVD SILICON-CONTAINING FILM APPLICATIONS

(71) Applicant: American Air Liquide, Inc., Fremont, CA (US)

(72) Inventors: Christian Dussarrat, Tokyo (JP); Glenn Kuchenbeiser, Newark, DE (US); Venkateswara R. Pallem, Hockessin, DE (US)

(73) Assignee: America Air Liquide, Inc., Fremont, CA (US)

( * ) Notice: Subject to any disclaimer, the term of this patent is extended or adjusted under 35 U.S.C. 154(b) by 137 days.

(21) Appl. No.: 14/415,647

(22) PCT Filed: Jul. 19, 2013

(86) PCT No.: PCT/US2013/051249
§ 371 (c)(1),
(2) Date: Jan. 19, 2015

(87) PCT Pub. No.: WO2014/015237
PCT Pub. Date: Jan. 23, 2014

(65) Prior Publication Data
US 2015/0166576 A1 Jun. 18, 2015

Related U.S. Application Data

(60) Provisional application No. 61/674,103, filed on Jul. 20, 2012.

(51) Int. Cl.
| | |
|---|---|
| *C07F 7/02* | (2006.01) |
| *C23C 16/30* | (2006.01) |
| *C23C 16/44* | (2006.01) |
| *C23C 16/34* | (2006.01) |
| *C23C 16/36* | (2006.01) |
| *C23C 16/40* | (2006.01) |
| *B05D 1/00* | (2006.01) |
| *H01L 21/02* | (2006.01) |
| *C23C 16/455* | (2006.01) |

(52) U.S. Cl.
CPC .............. *C07F 7/025* (2013.01); *B05D 1/60* (2013.01); *C23C 16/30* (2013.01); *C23C 16/345* (2013.01); *C23C 16/36* (2013.01); *C23C 16/401* (2013.01); *C23C 16/402* (2013.01); *C23C 16/44* (2013.01); *C23C 16/45553* (2013.01); *H01L 21/0228* (2013.01); *H01L 21/02216* (2013.01); *H01L 21/02271* (2013.01); *H01L 21/02532* (2013.01)

(58) Field of Classification Search
CPC ... C07F 7/025; C23C 16/45553; C23C 16/44; H01L 21/0228; H01L 21/02271; B05D 1/60
USPC .......................... 556/407; 427/248.1, 255.28
See application file for complete search history.

(56) References Cited

U.S. PATENT DOCUMENTS

| | | | |
|---|---|---|---|
| 2,590,039 A | 3/1952 | Richter et al. | |
| 3,355,477 A | 11/1967 | Frye | |
| 4,841,084 A | 6/1989 | Corriu et al. | |
| 5,394,269 A | 2/1995 | Takamatsu et al. | |
| 6,391,803 B1 | 5/2002 | Kim et al. | |
| 6,465,387 B1 | 10/2002 | Pinnavaia et al. | |
| 6,736,993 B1 | 5/2004 | Xu et al. | |
| 6,869,638 B2 | 3/2005 | Baum et al. | |
| 7,125,582 B2 | 10/2006 | McSwiney et al. | |
| 7,192,626 B2 | 3/2007 | Dussarrat et al. | |
| 7,332,618 B2 | 2/2008 | Meiere | |
| 7,482,286 B2 | 1/2009 | Misra et al. | |
| 7,875,312 B2 | 1/2011 | Thridandam et al. | |
| 8,129,555 B2 | 3/2012 | Cheng et al. | |
| 8,828,505 B2 | 9/2014 | Thridandam et al. | |
| 2006/0045986 A1 | 3/2006 | Hochberg et al. | |
| 2006/0258173 A1 | 11/2006 | Xiao et al. | |
| 2007/0160774 A1 | 7/2007 | Tsukada et al. | |
| 2007/0275166 A1 | 11/2007 | Thridandam et al. | |
| 2009/0302434 A1 | 12/2009 | Pallem et al. | |
| 2010/0112211 A1 | 5/2010 | Xu et al. | |
| 2010/0164057 A1 | 7/2010 | Hunks et al. | |
| 2010/0267979 A1* | 10/2010 | Bauer ................... | C07F 7/0829 556/479 |
| 2010/0317150 A1 | 12/2010 | Hunks et al. | |
| 2011/0045676 A1 | 2/2011 | Park et al. | |
| 2011/0061733 A1 | 3/2011 | Hurley et al. | |
| 2011/0250354 A1 | 10/2011 | Pallem et al. | |

(Continued)

FOREIGN PATENT DOCUMENTS

| | | |
|---|---|---|
| CN | 104341447 | 2/2015 |
| CN | 104341447 | 3/2015 |

(Continued)

OTHER PUBLICATIONS

Asay, M. et al., "N-heterocyclic carbene analogues with low-valent Group 13 and Group 14 elements: syntheses, structures, and reactivities of a new generation of multitalented ligands," Chem. Rev. 2011, 111, 354-396.

Herrmann, W.A. et al., "N-heterocyclic carbenes," Angew. Chem. Int. Ed. Engl. 1997, 36, 2162-2187.

Mattson, A.E. et al., "Thiazolium-catalyzed additions of acylsilanes: a general strategy for acyl anion addition reactions," J. Org. Chem. 2006, 71, 5715-5724.

Mück, F.M. et al., "Donor-stabilized silylenes with guanidinato ligands," Eur. J. Inorg. Chem. 2013, 5821-5825.

(Continued)

*Primary Examiner* — Porfirio Nazario Gonzalez
(74) *Attorney, Agent, or Firm* — Patricia E. McQueeney

(57) ABSTRACT

Disclosed are Si-containing thin film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

15 Claims, No Drawings

(56) References Cited

U.S. PATENT DOCUMENTS

| | | |
|---|---|---|
| 2012/0277457 A1 | 11/2012 | Lehmann et al. |
| 2013/0022745 A1 | 1/2013 | Dussarrat et al. |
| 2013/0078392 A1 | 3/2013 | Xiao et al. |
| 2014/0031502 A1 | 1/2014 | Qin et al. |
| 2015/0087139 A1 | 3/2015 | O'Neill et al. |

FOREIGN PATENT DOCUMENTS

| | | |
|---|---|---|
| EP | 1 310 500 | 5/2003 |
| EP | 1 563 117 | 2/2010 |
| EP | 2 154 141 | 2/2010 |
| EP | 2 392 691 | 12/2011 |
| EP | 2 444 405 | 4/2012 |
| JP | H06 132276 | 5/1994 |
| JP | H06 132284 | 5/1994 |
| JP | 2000 195801 | 7/2000 |
| KR | 2011 0009739 | 1/2011 |
| KR | 2012 0060843 | 6/2012 |
| KR | 10 2012 0078909 | 7/2012 |
| WO | WO 01 79578 | 10/2001 |
| WO | WO 2005 093126 | 10/2005 |
| WO | WO 2006 097525 | 9/2006 |
| WO | WO 2006 136584 | 12/2006 |
| WO | WO 2009 087609 | 7/2009 |
| WO | WO 2011 103282 | 8/2011 |
| WO | WO 2011 123792 | 10/2011 |
| WO | WO 2012 176988 | 12/2012 |
| WO | WO 2013 117326 | 11/2013 |
| WO | WO 2014 015232 | 1/2014 |
| WO | WO 2015 009997 | 1/2015 |

OTHER PUBLICATIONS

Naghammahmoodaljamali, "Review in cyclic compounds with heteroatom," Int. J. Curr. Res. Chem. Pharma. Sci. 1(9) (2014) 88-20.

Weidenbruch, M., "A stable silylenoid and a donor-stabilized chlorosilylene: low-coordinate silicon compounds—a never-ending story?," Angew. Chem. Int. Ed. 2006, 45, 4241-4242.

International Search Report and Written Opinion for corresponding PCT/US2015/065077, Aug. 10, 2016.

Baus, J.A. et al., "Neutral six-coordinate and cationic five-coordinate silicon(IV) complexes with two bidentate monoanionic N,S-pyridine-2-thiolato(-) ligands," Inorg. Chem, 2013, 52, 10664-10676.

Ebsworth, E.A.V. et al., "The preparation and properties of some silyl esters," J. Chem. Soc. (A), 1967, 69-72.

Eilingsfeld, H. et al., "Synthesen mit Amidchloriden, III. Synthese and Reaktionen von Chlorformamidiniumchloriden," Chemische Berichte vol. 97, Issue 5, May 1964, 1232-1245.

Gonzalez-Garcia et al., "Pentacoordinate mono(β-diketonato)- and hexacoordinate bis-(β-diketonato)-silicon(IV) complexes obtained from (thiocyanato-N)hydridosilanes," Polyhedron 41 (2012), 127-133.

Junold, K. et al., "Bis[N,N'-diisopropylbenzamidinato(-)]silicon(II): a silicon(II) compound with both a bidentate and a monodentate amidinato ligand," Angew. Chem. Int. Ed. 2012, 51, 7020-7023.

Junold, K. et al., "Novel neutral hexacoordinate benzamidinatosilicon(IV) complexes with $SiN_3OF_2$, $SiN_3OCl_2$, $SiN_3OBr_2$, $SiN_5O$ and $SiN_3O_3$ skeletons," Dalton Trans., 2011, 40, 9844-9857.

Karsch, H.H. et al., "Bis(amidinate) complexes of silicon and germanium," Eur. J. Inorg. Chem. 1998, 433-436.

Karsch, H.H. et al., "'Hypervalent' molecules—low valency candidates for materials?," Organosilicon Chemistry VI: From Molecules to Materials, N. Auner and J. Weis, eds., 2005, Wiley-VCH Verlag GmbH, Weinheim, 194-284.

Karsch, H.H. et al., "Silicon and germanium amidinates," Organosilicon Chemistry IV: From Molecules to Materials, N. Auner and J. Weis, eds., Wiley-VCH Verlag GmbH, Weinheim, Germany, 287-293.

Karsch, H.H. et al., "Silicon and germanium compounds with amidinate ligands," Organosilicon Chemistry V: From Molecules to Materials, N.. Auner and J. Weis, eds., 2003, Wiley-VCH Verlag GmbH, Weinheim, 270-276.

Negrebetsky, V.V. et al., "Dynamic stereochemistry of hypervalent silicon, germanium and tin compounds containing amidomethyl C,O-chelating ligands," Russian Chemical Bulleting, vol. 46, No. 11, Nov. 1997, 1807-1831.

Siddiqi, K.S. et al., "Group IV metal complexes of the dithiocarbamate ligand derived from propanediamine," Synthess and Reactivity in Inorganic and Metal-Organic chemistry, 23:5, 685-693.

Xu, C. et al., "Synthesis and characterization of neutral cis-hexacoordinate bis(β-diketonate) silicon(IV) complexes," Inorganic Chemistry 2004, 43, 1568-1573.

International Search Report and Written Opinion for corresponding PCT/US2013/051249, Oct. 16, 2013.

International Search Report and Written Opinion for related PCT/US2013/051244, Oct. 16, 2013.

International Search Report and Written Opinion for related PCT/US2013/051255, Oct. 16, 2013.

International Search Report and Written Opinion for related PCT/US2013/051264, Oct. 16, 2013.

Beckmann, J. et al., "The origin of ring strain and conformational flexibility in tri- and tetrasiloxane rings and their heavier Group 14 congeners," Organosilicon Chemistry VI: From Molecules to Materials, N. Auner and J. Weis, eds., 2005, Wiley-VCH Verlag GmbH, Weinheim, 252-258.

Dona, N. et al., "Novel dimeric pentacoordinate silicon complexes: unusual reactivity of electron-rich aminosilane intermediates," Organosilicon Chemistry VI: From Molecules to Materials, N. Auner and J. Weis, eds., 2005, Wiley-VCH Verlag GmbH, Weinheim, 271-278.

Dransfeld, A. et al., "The effect of silyl anion substituents on the stability and NMR characteristics of cyclic polyphosphines—an ab initio-NMR Study," Organosilicon Chemistry VI: From Molecules to Materials, N. Auner and J. Weis, eds., 2005, Wiley-VCH Verlag GmbH, Weinheim, 240-244.

von Frantzius, G. et al., "Strong evidence for an unconventional 1,2-(C->P)-silyl migration: DFT structures and bond strengths (compliance constants)," Organosilicon Chemistry VI: From Molecules to Materials, N. Auner and J. Weis, eds., 2005, Wiley-VCH Verlag GmbH, Weinheim, 211-215.

Hassler, K. et al., "Preparations and x-ray structures of some silicon-phosphorus and silicon-arsenic cages," Organosilicon Chemistry VI: From Molecules to Materials, N. Auner and J. Weis, eds., 2005, Wiley-VCH Verlag GmbH, Weinheim, 228-232.

Herzog, U. et al., "Si NMR chemical shift tensors in organosilicon chalcogenides," Organosilicon Chemistry VI: From Molecules to Materials, N. Auner and J. Weis, eds., 2005, Wiley-VCH Verlag GmbH, Weinheim, 259-264.

Ionescu, E. et al., "Strong evidence for an unconventional 1,2-(C->P)-silyl migration: formation and reactions of a P-silyl phosphaalkene complex," Organosilicon Chemistry VI: From Molecules to Materials, N. Auner and J. Weis, eds., 2005, Wiley-VCH Verlag GmbH, Weinheim, 202-208.

Lange, H. et al., "Hypersilyltelluro-substituted silanes and $(Ph_2SiTe)_3$," Organosilicon Chemistry VI: From Molecules to Materials, N. Auner and J. Weis, eds., 2005, Wiley-VCH Verlag GmbH, Weinheim, 265-270.

Kliem, S. et al., "Silyl group migrations between oxygen and nitrogen in aminosiloxanes," Organosilicon Chemistry VI: From Molecules to Materials, N. Auner and J. Weis, eds., 2005, Wiley-VCH Verlag GmbH, Weinheim, 216-221.

Mehring, M. et al., "Homo- and heterometallic bismuth silanolates," Organosilicon Chemistry VI: From Molecules to Materials, N. Auner and J. Weis, eds., 2005, Wiley-VCH Verlag GmbH, Weinheim, 233-239.

Pietschnig, R. et al., "Terphenyl phosphanosilanes," Organosilicon Chemistry VI: From Molecules to Materials, N. Auner and J. Weis, eds., 2005, Wiley-VCH Verlag GmbH, Weinheim, 222-227.

(56) References Cited

OTHER PUBLICATIONS

Veith, M. et al., "Silanols as precursors to cyclo- and polysiloxanes," Organosilicon Chemistry VI: From Molecules to Materials, N. Auner and J. Weis, eds., 2005, Wiley-VCH Verlag GmbH, Weinheim, 245-251.
Wagler, J. et al., "Unique switching of coordination number with imine and enamine complexes of Group 14 elements," Organosilicon Chemistry VI: From Molecules to Materials, N. Auner and J. Weis, eds , 2005, Wiley-VCH Verlag GmbH, Weinheim, 279-284.

* cited by examiner

ORGANOSILANE PRECURSORS FOR ALD/CVD SILICON-CONTAINING FILM APPLICATIONS

CROSS-REFERENCE TO RELATED APPLICATIONS

This application is a 371 of International PCT Application PCT/US2013/051249, filed Jul. 19, 2013, which claims priority to U.S. provisional application No. 61/674,103, filed Jul. 20, 2012, the entire contents of which are incorporated herein by reference.

TECHNICAL FIELD

Disclosed are Si-containing thin film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

BACKGROUND

Si-containing thin films are used widely in the semiconductor, photovoltaic, LCD-TFT, flat panel-type device, refactory material, or aeronautic industries. Si-containing thin films may be used, for example, as dielectric materials having electrical properties which may be insulating ($SiO_2$, SiN, SiCN, SiCOH, MSiOx, wherein M is Hf, Zr, Ti, Nb, Ta, or Ge and x is greater than zero), Si-containing thin films may be used as conducting films, such as metal silicides or metal silicon nitrides. Due to the strict requirements imposed by downscaling of electrical device architectures towards the nanoscale (especially below 28 nm node), increasingly fine-tuned molecular precursors are required which meet the requirements of volatility (for ALD process), lower process temperatures, reactivity with various oxidants and low film contamination, in addition to high deposition rates, conformality and consistency of films produced.

It is well known that silane ($SiH_4$) can be used for thermal CVD. However this molecule is pyrophoric which makes this room temperature gas a challenge to handle safely. CVD methods employing halosilanes (such as dichlorosilane $SiH_2Cl_2$) have been used. However, these may require long purge times, cause halogen contamination of the films and particle formation (from ammonium chloride salts), and even damage certain substrates resulting in undesirable interfacial layer formation. Partially replacing halogen with alkyl groups may yield some improvement, but at a cost of detrimental carbon contamination within the film.

Organoaminosilanes have been used as precursors for CVD of Si-containing films. U.S. Pat. No. 7,192,626 to Dussarrat et al. reports the use of trisilylamine $N(SiH_3)_3$ for deposition of SiN films. Other reported precursors include diisopropylaminosilane [$SiH_3(NiPr_2)$] and analogous $SiH_3(NR_2)$ compounds (see, e.g., U.S. Pat. No. 7,875,312 to Thridandam et al.) and phenylmethylaminosilane [$SiH_3(NPhMe)$] and related substituted silylanilines (see, e.g., EP 2392691 to Xiao et al.).

Another related class of Si precursors for CVD of Si-containing films is given by the general formula $(R^1R^2N)_x SiH_{4-x}$ wherein x is between 1 and 4 and the R substituents are independently H, C1-C6 linear, branched, or cyclic carbon chains (see, e.g., WO2006/097525 to Dussarrat et al.).

Hunks et al. disclose a wide range of Si-containing precursors in US2010/0164057, including silicon compounds having the formula $R_{4-x}SiL_x$, wherein x is an integer having a value from 1 to 3; R may be selected from H, branched and unbranched C1-C6 alkyl, C3-C8 cycloalkyl, and C6-C13 aryl groups; and L may be selected from isocyanato, methylethylketoxime, trifluoroacetate, triflate, acyloxy, β-diketiminate, β-di-iminate, amidinate, guanidinate, alkylamino, hydride, alkoxide, or formate ligands. Pinnavaia et al. claim a method for the preparation of a porous synthetic, semi-crystalline hybrid organic-inorganic silicon oxide composition from silicon acetylacetonate and silicon 1,3-diketonate precursors (U.S. Pat. No. 6,465,387).

Despite the wide range of choices available for the deposition of Si containing films, additional precursors are continuously sought to provide device engineers the ability to tune manufacturing process requirements and achieve films with desirable electrical and physical properties.

NOTATION AND NOMENCLATURE

Certain abbreviations, symbols, and terms are used throughout the following description and claims, and include:

As used herein, the indefinite article "a" or "an" means one or more.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR\%(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the term "aryl" refers to aromatic ring compounds where one hydrogen atom has been removed from the ring. As used herein, the term "heterocycle" refers to a cyclic compound that has atoms of at least two different elements as members of its ring.

As used herein, the abbreviation "Me" refers to a methyl group; the abbreviation "Et" refers to an ethyl group; the abbreviation "Pr" refers to any propyl group (i.e., n-propyl or isopropyl); the abbreviation "iPr" refers to an isopropyl group; the abbreviation "Bu" refers to any butyl group (n-butyl, iso-butyl, t-butyl, sec-butyl); the abbreviation "tBu" refers to a tert-butyl group; the abbreviation "sBu" refers to a sec-butyl group; the abbreviation "iBu" refers to an iso-butyl group; the abbreviation "Ph" refers to a phenyl group; the abbreviation "Am" refers to any amyl group (iso-amyl, sec-amyl, tert-amyl); the abbreviation "Hex" refers to a 6 member alkyl group, which may be linear, branched or cyclic; and the abbreviation "Cy" refers to a cyclic alkyl group (cyclobutyl, cyclopentyl, cyclohexyl, etc.).

As used herein, the acronym "SRO" stands for a Strontium Ruthenium Oxide film; the acronym "HCDS" stands for hexachlorodisilane; and the acronym "PODS" stands for pentachlorodisilane.

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

SUMMARY

Disclosed are organosilane molecules having the following formula:

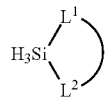

wherein each $L^1$ and $L^2$ is a nitrogen atom; $L^1$ and $L^2$ being joined together via a carbon bridge having two to three carbon atoms; $L^1$, $L^2$ and the carbon bridge forming a monoanionic ligand bonded to silicon. The disclosed molecules may have one or more of the following aspects:

the organosilane molecule having the following formula:

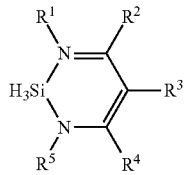

wherein $R^1$, $R^2$, $R^3$, $R^4$, and $R^5$ may each independently be H, a C1 to C6 alkyl group, or a C3-C20 aryl or heterocycle; $R^1$ and $R^2$ and/or $R^2$ and $R^3$ and/or $R^3$ and $R^4$ and/or $R^4$ and $R^5$ joined to form cyclic chains;

the organosilane molecule being $H_3Si(-(iPr)N—C_3H_3—N(iPr)-)$;

the organosilane molecule having the following formula:

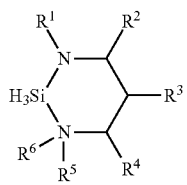

wherein $R^1$, $R^2$, $R^3$, $R^4$, $R^5$, and $R^6$ may each independently be H, a C1 to C6 alkyl group, or a C3-C20 aryl or heterocycle;

$R^1$ and $R^2$ and/or $R^2$ and $R^3$ and/or $R^3$ and $R^4$ and/or $R^4$ and $R^5$ and/or $R^5$ and $R^6$ joined to form cyclic chains;

the organosilane molecule being $H_3Si(-(iPr)N—C_3H_6—N(Me)_2-)$;

the organosilane molecule having the following formula:

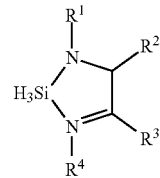

wherein $R^1$, $R^2$, $R^3$, $R^4$, and $R^5$ may each independently be H, a C1 to C6 alkyl group, or a C3-C20 aryl or heterocycle; $R^1$ and $R^2$ and/or $R^2$ and $R^3$ and/or $R^3$ and $R^4$ joined to form cyclic chains;

the organosilane molecule being $H_3Si(-(iPr)N—CH_2CH=N(iPr)-)$;

the organosilane molecule having the following formula:

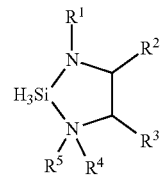

wherein $R^1$, $R^2$, $R^3$, $R^4$, and $R^5$ may each independently be H, a C1 to C6 alkyl group, or a C3-C20 aryl or heterocycle; $R^1$ and $R^2$ and/or $R^2$ and $R^3$ and/or $R^3$ and $R^4$ and/or $R^4$ and $R^5$ joined to form cyclic chains; and the organosilane molecule being $H_3Si((iPr)NC_2H_4N(Me)_2$.

Also disclosed are Si-containing thin film forming precursors having the following formula:

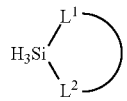

wherein each $L^1$ and $L^2$ is a nitrogen atom; $L^1$ and $L^2$ being joined together via a carbon bridge having two to three carbon atoms; $L^1$, $L^2$ and the carbon bridge forming a monoanionic ligand bonded to silicon. The disclosed molecules may have one or more of the following aspects:

the Si-containing thin film forming precursor having the following formula:

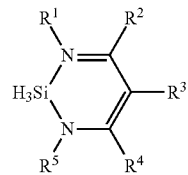

wherein $R^1$, $R^2$, $R^3$, $R^4$, and $R^5$ may each independently be H, a C1 to C6 alkyl group, or a C3-C20 aryl or heterocycle; $R^1$ and $R^2$ and/or $R^2$ and $R^3$ and/or $R^3$ and $R^4$ and/or $R^4$ and $R^5$ joined to form cyclic chains;

the Si-containing thin film forming precursor being $H_3Si(-(iPr)N—C_3H_3—N(iPr)-)$;

the Si-containing thin film forming precursor having the following formula:

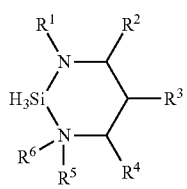

wherein $R^1$, $R^2$, $R^3$, $R^4$, $R^5$, and $R^6$ may each independently be H, a C1 to C6 alkyl group, or a C3-C20 aryl or heterocycle;
  $R^1$ and $R^2$ and/or $R^2$ and $R^3$ and/or $R^3$ and $R^4$ and/or $R^4$ and $R^5$ and/or $R^5$ and $R^6$ joined to form cyclic chains;
  the Si-containing thin film forming precursor being $H_3Si$(-(iPr)N—$C_3H_6$—N(Me)$_2$-);
  the Si-containing thin film forming precursor having the following formula:

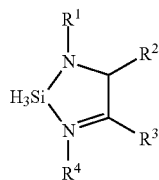

wherein $R^1$, $R^2$, $R^3$, $R^4$, and $R^5$ may each independently be H, a C1 to C6 alkyl group, or a C3-C20 aryl or heterocycle;
  $R^1$ and $R^2$ and/or $R^2$ and $R^3$ and/or $R^3$ and $R^4$ joined to form cyclic chains;
  the Si-containing thin film forming precursor being $H_3Si$(-(iPr)N—$CH_2CH$=N(iPr)-);
  the Si-containing thin film forming precursor having the following formula:

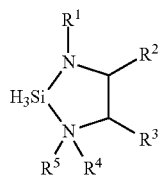

wherein $R^1$, $R^2$, $R^3$, $R^4$, and $R^5$ may each independently be H, a C1 to C6 alkyl group, or a C3-C20 aryl or heterocycle;
  $R^1$ and $R^2$ and/or $R^2$ and $R^3$ and/or $R^3$ and $R^4$ and/or $R^4$ and $R^5$ joined to form cyclic chains; and
  the Si-containing thin film forming precursor being $H_3Si$((iPr)N$C_2H_4$N(Me)$_2$.
  Also disclosed are methods of depositing a Si-containing layer on a substrate.
  At least one organosilane precursor disclosed above is introduced into a reactor having at least one substrate disposed therein. At least part of the organosilane precursor is deposited onto the at least one substrate to form a Si-containing layer using a vapor deposition method. The disclosed methods may have one or more of the following aspects:
    introducing into the reactor a vapor comprising at least one second precursor;
    an element of the at least one second precursor being selected from the group consisting of group 2, group 13, group 14, transition metal, lanthanides, and combinations thereof;
    the element of the at least one second precursor being selected from Mg, Ca, Sr, Ba, Zr, Hf, Ti, Nb, Ta, Al, Si, Ge, Y, or lanthanides;
    introducing into the reactor at least one co-reactant;
    the co-reactant being selected from the group consisting of $O_2$, $O_3$, $H_2O$, $H_2O_2$, NO, $NO_2$, a carboxylic acid, radicals thereof, and combinations thereof;
    the co-reactant being plasma treated oxygen;
    the co-reactant being ozone;
    the Si-containing layer being a silicon oxide layer;
    the co-reactant being selected from the group consisting of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkysilanes (such as $Me_2SiH_2$, $Et_2SiH_2$, $MeSiH_3$, $EtSiH_3$), hydrazines (such as $N_2H_4$, $MeHNNH_2$, MeHNNHMe), organic amines (such as $NMeH_2$, $NEtH_2$, $NMe_2H$, $NEt_2H$, $NMe_3$, $NEt_3$, $(SiMe_3)_2NH$), pyrazoline, pyridine, B-containing molecules (such as $B_2H_6$, 9-borabicylo[3,3,1]none, trimethylboron, triethylboron, borazine), alkyl metals (such as trimethylaluminum, triethylaluminum, dimethylzinc, diethylzinc), radical species thereof, and mixtures thereof.
    the co-reactant being selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;
    the co-reactant being plasma-treated;
    the co-reactant being remote plasma-treated;
    the co-reactant not being plasma-treated;
    the co-reactant being $H_2$;
    the co-reactant being $NH_3$;
    the co-reactant being HCDS;
    the co-reactant being PODS;
    the co-reactant being tetrachlorosilane;
    the co-reactant being trichlorosilane;
    the co-reactant being hexachlorocyclohexasilane;
    the vapor deposition process being a chemical vapor deposition process;
    the vapor deposition process being an atomic layer deposition (ALD) process;
    the vapor deposition processing being a spatial ALD process;
    the silicon-containing layer being Si;
    the silicon-containing layer being $SiO_2$;
    the silicon-containing layer being SiN;
    the silicon-containing layer being SiON;
    the silicon-containing layer being SiCN; and
    the silicon-containing layer being SiCOH.

DESCRIPTION OF PREFERRED EMBODIMENTS

Disclosed are Si-containing thin film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

The disclosed Si-containing thin film forming precursors have the following formula:

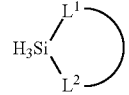

wherein each $L^1$ and $L^2$ is a nitrogen atom, $L^1$ and $L^2$ being joined together via a carbon bridge having two or three carbon atoms; $L^1$, $L^2$, and the carbon bridge form a monoanionic ligand bonded to silicon. As illustrated in the formula, the $L^1$ and $L^2$ nitrogen atoms are bonded to the silicon atom, resulting in a pentacoordinate Si(IV) center. The carbon atoms in the carbon bridge may be $sp^2$ hybridized, resulting in a delocalized charge across the monoanionic ligand. Alternatively, the carbon atoms in the carbon bridge may be either sp3 hybridized or some combination of sp2 and sp3 hybridized, resulting in a negative charge on one of $L^1$ or $L^2$ and resulting in a neutral charge on the other of $L^1$ or $L^2$. Each of the nitrogen and carbon atoms may independently be substituted by H, C1-C6 alkyl groups, aryl groups, or heterocycle groups.

The disclosed organosilane precursors may be more reactive than other $R_{4-x}SiL_x$ precursors due to hypercoordination at the silicon atom. In other words, although the silicon atom is +IV, the three hydrogen bonds and the monoanionic chelating ligand results in a total of 5 bonds to the silicon atom.

Due to their increased nitrogen content on the N—(C)n-N ligand, with n being 2 or 3, these molecules may be used to produce silicon-containing films that also contain nitrogen, such as SiN, SiCN, SiON, MSiN, or MSiON, wherein M is an element such as Hf, Zr, Ti, Nb, Ta, or Ge, or to tune the amount of nitrogen in those films.

When the carbon bridge of the disclosed organosilane precursors includes three (3) carbon atoms (i.e., —N—(C(R))₃—N—), the resulting precursors are 3-diketiminatosilane compounds. Exemplary β-diketiminatosilane precursors have the following formula:

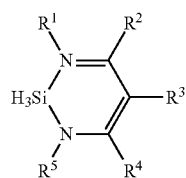

wherein $R^1$, $R^2$, $R^3$, $R^4$, and $R^5$ may each independently be H, a C1 to C6 alkyl group, or a C3-C20 aryl or heterocycle $R^1$ and $R^2$ and/or $R^2$ and $R^3$ and/or $R^3$ and $R^4$ and/or $R^4$ and $R^5$ may be joined to form cyclic chains. The three carbon atoms are $sp^2$ hybridized. If $R^1$ and $R^5$ are the same and $R^2$ and $R^4$ are the same (i.e., all Me, or $R^1$ and $R^5$=Me and $R^2$ and $R^4$=H), the resulting Fourier-Transform Infra Red (FTIR) spectra for these molecules will produce one peak for both of the N atoms due to the delocalization of the electrons across the ligand.

Exemplary β-diketiminatosilane precursors with the above formula include:

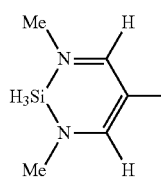 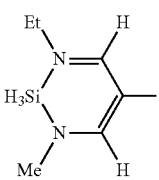 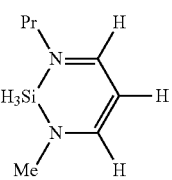

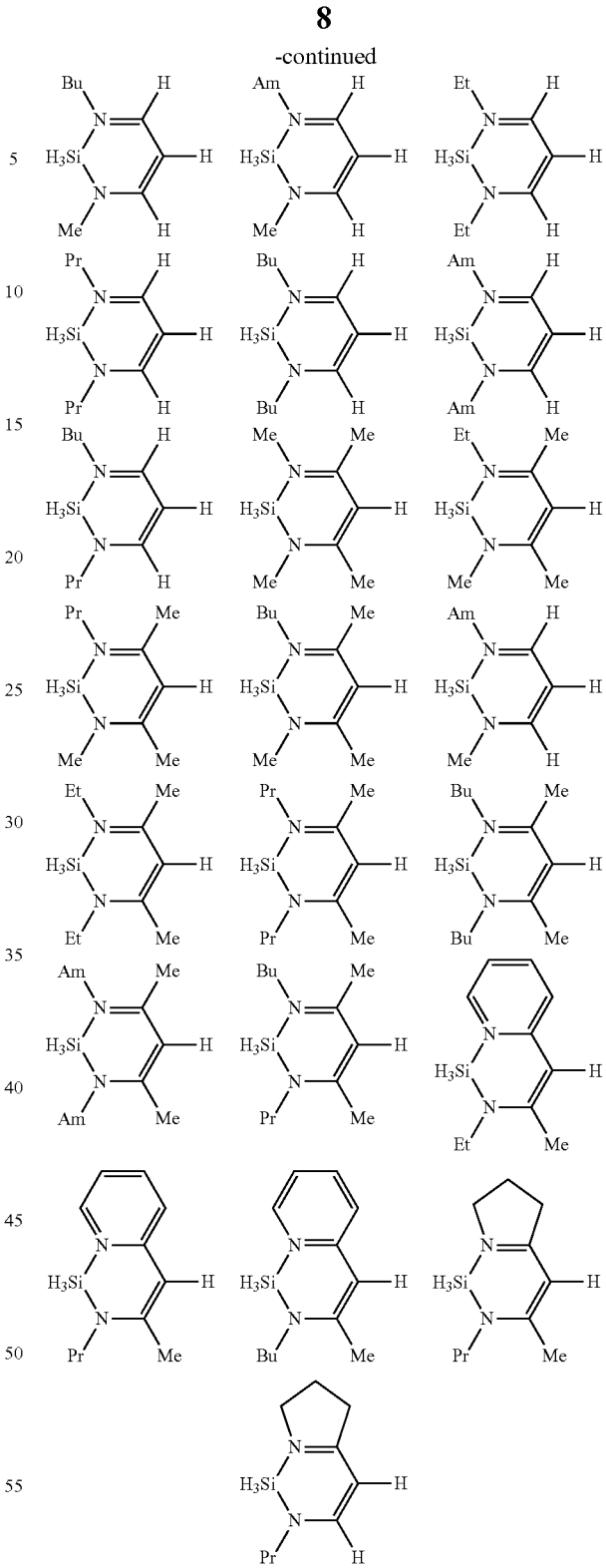

Preferably, the β-diketiminatosilane precursor is H₃Si(-(iPr)N—C₃H₃—N(iPr)-).

When the carbon bridge of the disclosed organosilane precursors includes three (3) carbon atoms (i.e., —N—(C(R))₃—N—), the resulting precursors are aminosilylamine compounds. Exemplary aminosilylamine organosilane precursors have the following formula:

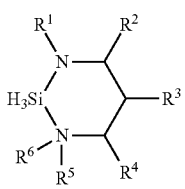

wherein $R^1$, $R^2$, $R^3$, $R^4$, $R^5$, and $R^6$ may each independently be H, a C1 to C6 alkyl group, or a C3-C20 aryl or heterocycle. One of ordinary skill in the art will recognize the implied H on the carbons in the structure above, which has been left off due to space constraints. $R^1$ and $R^2$ and/or $R^2$ and $R^3$ and/or $R^3$ and $R^4$ and/or $R^4$ and $R^5$ and/or $R^5$ and $R^6$ may be joined to form cyclic chains. The three carbon atoms may be sp2 or sp3 hybridized. An anionic charge may be localized at the "top" nitrogen atom. The "bottom" nitrogen atom may form a dative bond to the Si atom. Due to the unsymmetrical nature of the ligand, the three carbon atoms will produce different peaks in nuclear magnetic resonance (NMR) spectra.

Exemplary aminosilylamine precursors with the above formula include:

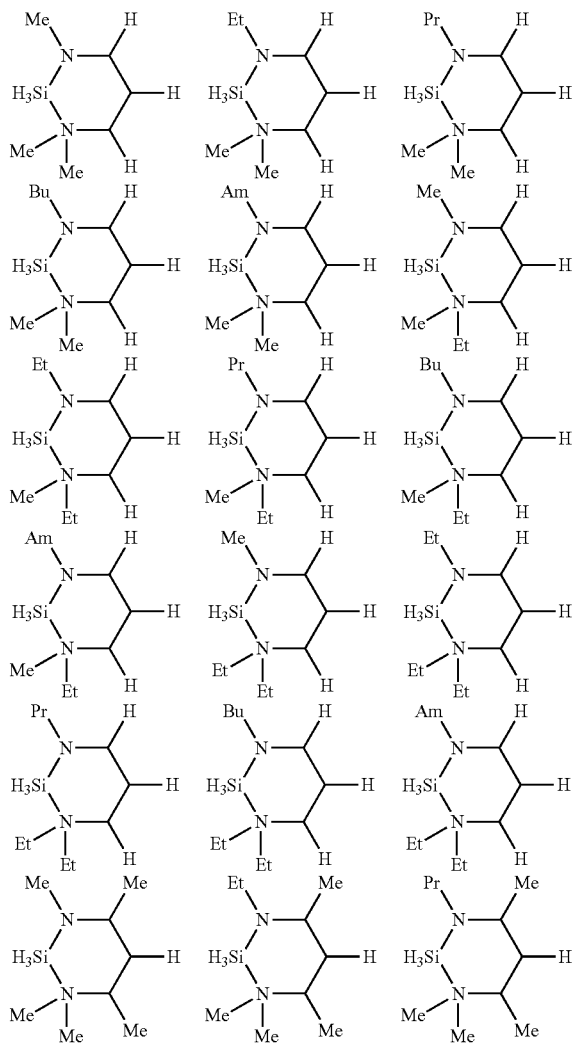

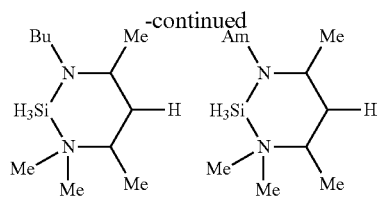

Preferably, the aminosilylamine precursor is $H_3Si(-(iPr)N-C_3H_6-N(Me)_2-)$.

The $H_3Si[RN(CR)_3NR]$ or $H_3Si[R_2N(CR)_3NR]$ precursors may be synthesized by combining a hydrocarbon solution of $SiXH_3$, wherein X is Cl, Br, I, or triflate ($SO_3CF_3^-$), with a neat or hydrocarbon solution of the ligand compound, such as $Li[RN(CR)_3NR]$ or $Li[R_2N(CR)_3NR]$, under atmosphere of nitrogen, the outlet of the mixing flask being connected to an oil bubbler to inhibit backflow of air and moisture.

A second synthetic route to the disclosed $H_3Si[RN(CR)_3NR]$ or $H_3Si[R_2N(CR)_3NR]$ precursors is by reaction of the protonated ligand $RN(CR)_3NHR$ or $RHN(CR)_3NR_2$ with either a neat or a hydrocarbon solution of a dialkylaminosilane $[SiH_3(NR_2)]$ performed under an inert atmosphere.

Alternatively, the disclosed $H_3Si[RN(CR)_3NR]$ or $H_3Si[R_2N(CR)_3NR]$ precursors may be synthesized by reaction of $SiH_nCl_{4-n}$ with a single equivalent of the ligand compound (i.e., $Li[RN(CR)_3NR]$ or $Li[R_2N(CR)_3NR]$) and subsequent reduction using a selected metal hydride, such as LAH (lithium aluminum hydride).

In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[RN(CR)_3NR]$ or $Li[R_2N(CR)_3NR]$, all of the starting materials are commercially available. The ligand compound may be synthesized by combining a hydrocarbon solution of metalorganic salt (i.e., alkyl lithium) to a hydrocarbon solution of the appropriate diamine (i.e., $R^1N=CR^2-CR^3-CR^4-NHR^5$, $R^1N=CR^2-CR^3=CR^4-NHR^5$, $R^1HN-CR^2-CR^3-CR^4-NR^5R^6$). One of ordinary skill in the art would recognize that proper selection of the ligand will result in the unsaturated β-diketiminatosilane precursor or the saturated aminosilylamine precursor.

When the carbon bridge of the disclosed organosilane precursors includes two (2) carbon atoms (i.e., $-N-(C(R))_2-N-$, the resulting precursors are iminosilylamine compounds. Exemplary iminosilylamine organosilane precursors have the following formula:

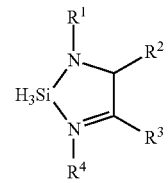

wherein $R^1$, $R^2$, $R^3$, and $R^4$ may each independently be H, a C1 to C6 alkyl group, or a C3-C20 aryl or heterocycle. One of ordinary skill in the art will recognize the implied H on the carbon in the structure above, which has been left off due to space constraints. $R^1$ and $R^2$ and/or $R^2$ and $R^3$ and/or $R^3$ and $R^4$ may be joined to form cyclic chains. The two carbon atoms may be $sp^2$ or $sp^a$ hybridized. The formula above illustrates an anionic charge localized at the "top" nitrogen atom. The "bottom" nitrogen atom having the double bond to $C(R^3)$ forms a dative bond to the silicon atom. However, one of ordinary skill in the art will recognize that the double bond may also be delocalized across the ring when the carbon atoms are $sp^2$ hybridized. If $R^1$ and $R^4$ are the same and $R^2$ and $R^3$ are the same (i.e., all Me, or $R^1$ and $R^4$=Me and $R^2$ and $R^3$=H), the resulting Fourier-transform Infra Red (FTIR) spectra for these molecules will produce one peak for both of the N atoms due to the delocalization of the electrons across the ligand.

Exemplary iminosilylamine precursors with the above formula include:

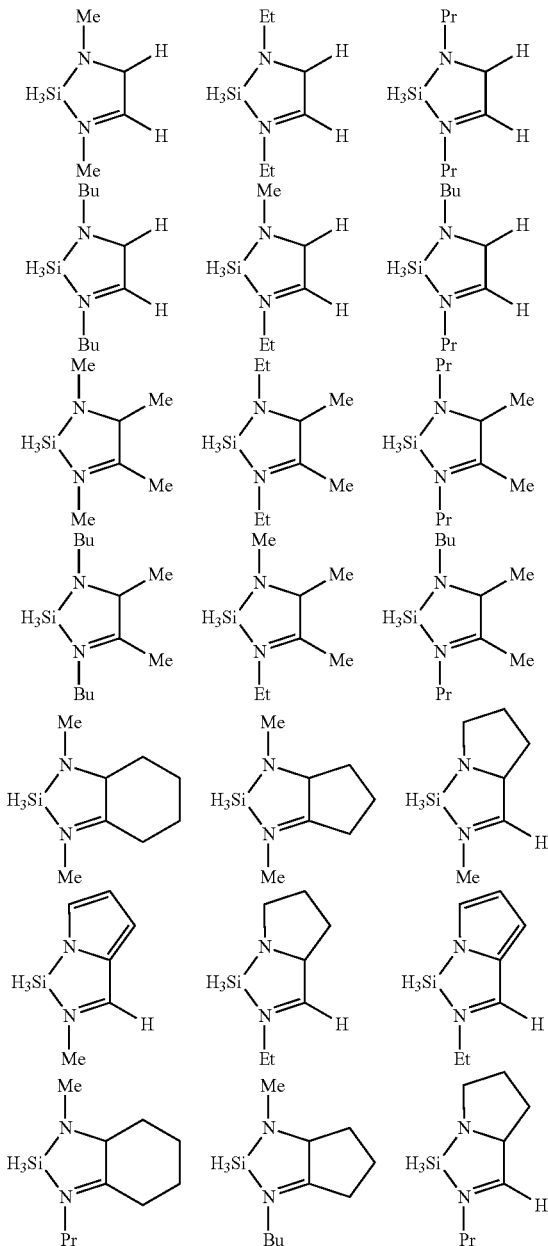

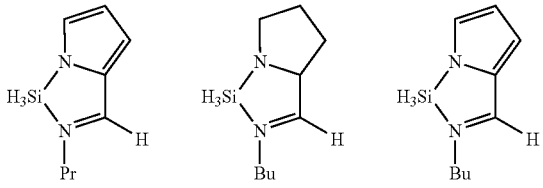

Preferably the iminosilylamine is $H_3Si(-(iPr)N-CH_2CH=N(iPr)-)$.

When the carbon bridge of the disclosed organosilane precursors includes two (2) carbon atoms (i.e., $-N-(C(R))_2-N-$, the resulting precursors are aminosilylamine compounds. Exemplary aminosilylamine organosilane precursors have the following formula:

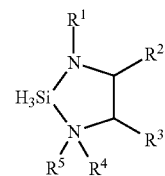

wherein $R^1$, $R^2$, $R^3$, $R^4$, and $R^5$ may each independently be H, a C1 to C6 alkyl group, or a C3-C20 aryl or heterocycle. One of ordinary skill in the art will recognize the implied H on the carbons in the structure above, which have been left off due to space constraints. $R^1$ and $R^2$ and/or $R^2$ and $R^3$ and/or $R^3$ and $R^4$ and/or $R^4$ and $R^5$ may be joined to form cyclic chains. The two carbon atoms may be sp2 or sp3 hybridized. An anionic charge may be localized at the nitrogen atom. The other nitrogen atom may form a dative bond to the Si atom. Due to the unsymmetrical nature of the ligand, the two carbon atoms will produce different peaks in nuclear magnetic resonance (NMR) spectra.

Exemplary aminosilylamine precursors with the above formula include:

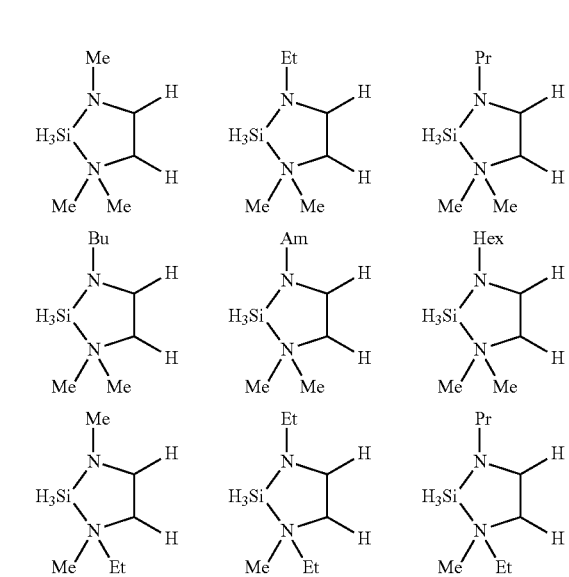

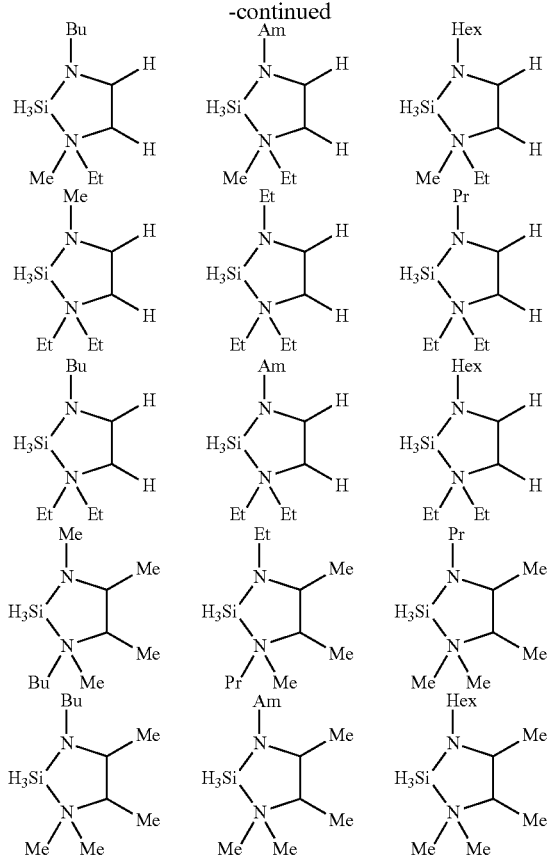

Preferably, the aminosilylamine precursor is $H_3Si((iPr)NC_2H_4N(Me)_2)$.

The $H_3Si[RN(CR)_2NR]$ or $H_3Si[R_2N(CR)_2NR]$ precursors may be synthesized by combining a hydrocarbon solution of $SiXH_3$, wherein X is Cl, Br, I, or triflate ($SO_3CF_3$), with a neat or hydrocarbon solution of the ligand compound, such as $Li[RN(CR)_2NR]$ or $Li[R_2N(CR)_2NR]$, under atmosphere of nitrogen, the outlet of the mixing flask being connected to an oil bubbler to inhibit backflow of air and moisture.

A second synthetic route to the disclosed $H_3Si[RN(CR)_2NR]$ or $H_3Si[R_2N(CR)_2NR]$ precursors is by reaction of the protonated ligand $RN(CR)_2NHR$ or $RHN(CR)_2NR_2$ with either a neat or a hydrocarbon solution of a dialkylaminosilane $[SiH_3(NR_2)]$ performed under an inert atmosphere.

Alternatively, the disclosed $H_3Si[RN(CR)_2NR]$ or $H_3Si[R_2N(CR)_2NR]$ precursors may be synthesized by reaction of $SiH_nCl_4$, with a single equivalent of the ligand compound (i.e., $Li[RN(CR)_2NR]$ or $Li[R_2N(CR)_2NR]$) and subsequent reduction using a selected metal hydride, such as LAH (lithium aluminum hydride).

In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds $Li[RN(CR)_2NR]$ or $Li[R_2N(CR)_2NR]$, all of the starting materials are commercially available. The ligand compound may be synthesized by combining a hydrocarbon solution of metalorganic salt (i.e., alkyl lithium) to a hydrocarbon solution of the appropriate diamine (i.e., $R^1N=CR^2-CR^3-NHR^4$, $R^1HN-CR^2-CR^3-NR^4R^5$). One of ordinary skill in the art would recognize that proper selection of the ligand will result in the saturated aminosilylamino or unsaturated iminosilylamino precursor.

Also disclosed are methods of using the disclosed organosilane precursors for vapor deposition methods. The disclosed methods provide for the use of the organosilane precursors for deposition of silicon-containing films. The disclosed methods may be useful in the manufacture of semiconductor, photovoltaic, LCD-TFT, or flat panel type devices. The method includes: providing a substrate; providing a vapor including at least one of the disclosed organosilane precursors; and contacting the vapor with the substrate (and typically directing the vapor to the substrate) to form a silicon-containing layer on at least one surface of the substrate.

The disclosed methods also provide for forming a bimetal-containing layer on a substrate using a vapor deposition process and, more particularly, for deposition of $SiMO_x$ films, wherein x may be 0-4 and M is Ta, Hf, Nb, Mg, Al, Sr, Y, Ba, Ca, As, Sb, Bi, Sn, Pb, Co, lanthanides (such as Er), or combinations thereof. The disclosed methods may be useful in the manufacture of semiconductor, photovoltaic, LCD-TFT, or flat panel type devices. The method includes: providing a substrate; providing a vapor including at least one of the disclosed organosilane precursors and contacting the vapor with the substrate (and typically directing the vapor to the substrate) to form a bi metal-containing layer on at least one surface of the substrate. An oxygen source, such as $O_3$, $O_2$, $H_2O$, NO, $H_2O_2$, acetic acid, formalin, paraformaldehyde, oxygen radicals thereof, and combinations thereof, but preferably $O_3$ or plasma treated $O_2$ may also be provided with the vapor.

The disclosed organosilane precursors may be used to deposit silicon-containing films using any deposition methods known to those of skill in the art. Examples of suitable deposition methods include without limitation, conventional chemical vapor deposition (CVD), low pressure chemical vapor deposition (LPCVD), atomic layer deposition (ALD), pulsed chemical vapor deposition (P-CVD), thermal ALD, thermal CVD, plasma enhanced atomic layer deposition (PE-ALD), plasma enhanced chemical vapor deposition (PE-CVD), spatial ALD, or combinations thereof. Preferably, the deposition method is ALD, spatial ALD, or PE-ALD.

The vapor of the organosilane precursor is introduced into a reaction chamber containing at least one substrate. The temperature and the pressure within the reaction chamber and the temperature of the substrate are held at conditions suitable for vapor deposition of at least part of the organosilane precursor onto the substrate. In other words, after introduction of the vaporized precursor into the chamber, conditions within the chamber are such that at least part of the vaporized precursor is deposited onto the substrate to form the silicon-containing film. A co-reactant may also be used to help in formation of the Si-containing layer.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr to about 20 Torr. In addition, the temperature within the reaction chamber may range from about 20° C. to about 600° C. One of ordinary skill in the art will recognize that the temperature may be optimized through mere experimentation to achieve the desired result.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 300° C. to approximately 600° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 150° C. to 600° C. Preferably, the temperature of the substrate remains less than or equal to 500° C.

The type of substrate upon which the silicon-containing film will be deposited will vary depending on the final use intended. In some embodiments, the substrate may be a patterned photoresist film made of hydrogenated carbon, for example $CH_x$, wherein x is greater than zero. In some embodiments, the substrate may be chosen from oxides which are used as dielectric materials in MIM, DRAM, or FeRam technologies (for example, $ZrO_2$ based materials, $HfO_2$ based materials, $TiO_2$ based materials, rare earth oxide based materials, ternary oxide based materials, etc.) or from nitride-based films (for example, TaN) that are used as an oxygen barrier between copper and the low-k layer. Other substrates may be used in the manufacture of semiconductors, photovoltaics, LCD-TFT, or flat panel devices. Examples of such substrates include, but are not limited to, solid substrates such as metal nitride containing substrates (for example, TaN, TiN, WN, TaCN, TiCN, TaSiN, and TiSiN); insulators (for example, $SiO_2$, $Si_3N_4$, SiON, $HfO_2$, $Ta_2O_5$, $ZrO_2$, $TiO_2$, $Al_2O_3$, and barium strontium titanate); or other substrates that include any number of combinations of these materials. The actual substrate utilized may also depend upon the specific precursor embodiment utilized. In many instances though, the preferred substrate utilized will be selected from hydrogenated carbon, TiN, SRO, Ru, and Si type substrates, such as polysilicon or crystalline silicon substrates.

The disclosed organosilane precursors may be supplied either in neat form or in a blend with a suitable solvent, such as toluene, ethyl benzene, xylene, mesitylene, decane, dodecane, octane, hexane, pentane, tertiary amines, acetone, tetrahydrofuran, ethanol, ethylmethylketone, 1,4-dioxane, or others. The disclosed precursors may be present in varying concentrations in the solvent. For example, the resulting concentration may range from approximately 0.05 M to approximately 2 M.

The neat or blended organosilane precursors are introduced into a reactor in vapor form by conventional means, such as tubing and/or flow meters. The precursor in vapor form may be produced by vaporizing the neat or blended precursor solution through a conventional vaporization step such as direct vaporization, distillation, by bubbling, or by using a sublimator such as the one disclosed in PCT Publication WO2009/087609 to Xu et al. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling the carrier gas into the precursor. The carrier gas may include, but is not limited to, Ar, He, or $N_2$, and mixtures thereof. Bubbling with a carrier gas may also remove any dissolved oxygen present in the neat or blended precursor solution. The carrier gas and precursor are then introduced into the reactor as a vapor.

If necessary, the container may be heated to a temperature that permits the organosilane precursor to be in its liquid phase and to have a sufficient vapor pressure. The container may be maintained at temperatures in the range of, for example, 0-150° C. Those skilled in the art recognize that the temperature of the container may be adjusted in a known manner to control the amount of organosilane precursor vaporized.

In addition to the disclosed precursor, a reaction gas may also be introduced into the reactor. The reaction gas may be an oxidizing agent such as one of $O_2$; $O_3$; $H_2O$; $H_2O_2$; oxygen containing radicals such as O. or OH.; NO; $NO_2$; carboxylic acids such as formic acid, acetic acid, propionic acid; radical species of NO, $NO_2$, or the carboxylic acids; para-formaldehyde; and mixtures thereof. Preferably, the oxidizing agent is selected from the group consisting of $O_2$, $O_3$, $H_2O$, $H_2O_2$, oxygen containing radicals thereof such as O. or OH., and mixtures thereof. Preferably, when an ALD process is performed, the co-reactant is plasma treated oxygen, ozone, or combinations thereof. When an oxidizing gas is used, the resulting silicon containing film will also contain oxygen.

Alternatively, the reaction gas may be a reducing agent such as one of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SIH_3Cl$, $Si_2Cl_6$, $Si_2HCl_5$, $Si_3Cl_8$), alkylsilanes (such as $(CH_3)_2SiH_2$, $(C_2H_5)_2SiH_2$, $(CH_3)SiH_3$, $(C_2H_5)SiH_3$), hydrazines (such as $N_2H_4$, $MeHNNH_2$, MeHNNHMe), organic amines (such as $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$), pyrazoline, pyridine, B-containing molecules (such as $B_2H_6$, 9-borabicyclo[3,3,1]none, trimethylboron, triethylboron, borazine), alkyl metals (such as trimethylaluminum, triethylaluminum, dimethylzinc, diethylzinc), radical species thereof, and mixtures thereof. Preferably, the reducing agent is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof. When a reducing agent is used, the resulting silicon containing film may be pure Si.

The reaction gas may be treated by a plasma, in order to decompose the reaction gas into its radical form. $N_2$ may also be utilized as a reducing agent when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The disclosed organosilane precursors may also be used with a halosilane or polyhalodisilane, such as hexachlorodisilane, pentachlorodisilane, or tetrachlorodisilane, and one or more co-reactant gases to form SiN and SiCN films, as disclosed in PCT Publication Number WO2011/123792, the entire contents of which are incorporated herein in their entireties.

When the desired silicon-containing film also contains another element, such as, for example and without limitation, Ta, Hf, Nb, Mg, Al, Sr, Y, Ba, Ca, As, Sb, Bi, Sn, Pb, Co, lanthanides (such as Er), or combinations thereof, the co-reactants may include a metal-containing precursor which is selected from, but not limited to, metal alkyls, such as $Ln(RCp)_3$ or $Co(RCp)_2$, metal amines, such as $Nb(Cp)(NtBu)(NMe_2)_3$ and any combination thereof.

The organosilane precursor and one or more co-reactants may be introduced into the reaction chamber simultaneously (chemical vapor deposition), sequentially (atomic layer deposition), or in other combinations. For example, the organosilane precursor may be introduced in one pulse and two additional metal sources may be introduced together in a separate pulse [modified atomic layer deposition]. Alternatively, the reaction chamber may already contain the co-reactant prior to introduction of the organosilane precursor. The co-reactant may be passed through a plasma system localized or remotely from the reaction chamber, and decomposed to radicals. Alternatively, the organosilane precursor may be introduced to the reaction chamber continuously while other metal sources are introduced by pulse (pulsed-chemical vapor deposition). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s. In another alternative, the organosilane precursor and one or more co-reactants may be simultaneously sprayed from a shower head under which a susceptor holding several wafers is spun (spatial ALD).

In one non-limiting exemplary atomic layer deposition type process, the vapor phase of an organosilane precursor is introduced into the reaction chamber, where it is contacted with a suitable substrate. Excess organosilane precursor may then be removed from the reaction chamber by purging and/or evacuating the reaction chamber. An oxygen source is introduced into the reaction chamber where it reacts with the absorbed organosilane precursor in a self-limiting manner. Any excess oxygen source is removed from the reaction chamber by purging and/or evacuating the reaction chamber. If the desired film is a silicon oxide film, this two-step process may provide the desired film thickness or may be repeated until a film having the necessary thickness has been obtained.

Alternatively, if the desired film is a silicon metal oxide film (i.e., $SiMO_x$, wherein and x may be 0-4 and M is Ta, Hf, Nb, Mg, Al, Sr, Y, Ba, Ca, As, Sb, Bi, Sn, Pb, Co, lanthanides (such as Er), or combinations thereof), the two-step process above may be followed by introduction of a second vapor of a metal-containing precursor into the reaction chamber. The metal-containing precursor will be selected based on the nature of the silicon metal oxide film being deposited. After introduction into the reaction chamber, the metal-containing precursor is contacted with the substrate. Any excess metal-containing precursor is removed from the reaction chamber by purging and/or evacuating the reaction chamber. Once again, an oxygen source may be introduced into the reaction chamber to react with the metal-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the organosilane precursor, metal-containing precursor, and oxygen source, a film of desired composition and thickness can be deposited.

Additionally, by varying the number of pulses, films having a desired stoichiometric M:Si ratio may be obtained. For example, a $SiMO_2$ film may be obtained by having one pulse of the organosilane precursor and one pulses of the metal-containing precursor, with each pulse being followed by pulses of the oxygen source. However, one of ordinary skill in the art will recognize that the number of pulses required to obtain the desired film may not be identical to the stoichiometric ratio of the resulting film.

In another alternative, Si or dense SiCN films may be deposited via an ALD or modified ALD process using the disclosed compounds and a halosilane compound having the formula $Si_aH_{2a+2-b}X_b$, wherein X is F, Cl, Br, or I; a=1 through 6; and b=1 through (2a+2); or a cyclic halosilane compound having the formula $—Si_cH_{2c-d}X_d—$, wherein X is F, Cl, Br, or I; c=3-8; and d=1 through 2c. Preferably the halosilane compound is trichlorosilane, hexachlorodisilane (HCDS), pentachlorodisilane (PODS), tetrachlorodisilane, or hexachlorocyclohexasilane. One of ordinary skill in the art will recognize that the Cl in these compounds may be substituted by Br or I when lower deposition temperatures are necessary, due to the lower bond energy in the Si—X bond (i.e., Si—Cl=456 kJ/mol; Si—Br=343 kJ/mol; Si—I=339 kJ/mol). If necessary, the deposition may further utilize an N-containing co-reactant, such as $NH_3$. Vapors of the disclosed precursors and the halosilane compounds may be introduced sequentially or simultaneously into the reactor, depending on the desired concentration of the final film. The selected sequence of precursor injection will be determined based upon the desired film composition targeted. The precursor introduction steps may be repeated until the deposited layer achieves a suitable thickness. One of ordinary skill in the art will recognize that the introductory pulses may be simultaneous when using a spatial ALD device. As described in PCT Pub No WO2011/123792, the order of the introduction of the precursors may be varied and the deposition may be performed with or without the $NH_3$ co-reactant in order to tune the amounts of carbon and nitrogen in the SiCN film.

The silicon-containing films resulting from the processes discussed above may include $SiO_2$, SiN, SiON, SiCN, SiCOH, or $MSiO_x$, wherein M is an element such as Hf, Zr, Ti, Nb, Ta, or Ge, and x may be 4, depending of course on the oxidation state of M. One of ordinary skill in the art will recognize that by judicial selection of the appropriate organosilane precursor and co-reactants, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the silicon-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an 0-containing atmosphere, or combinations thereof. Most preferably, the temperature is 600° C. for less than 3600 seconds under a H-containing atmosphere. The resulting film may contain fewer impurities and therefore may have improved performance characteristics. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the silicon-containing film.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A Si-containing thin film forming precursor having the following formula:

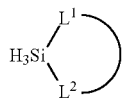

wherein each $L^1$ and $L^2$ is a nitrogen atom; $L^1$ and $L^2$ being joined together via a carbon bridge having two to three carbon atoms; $L^1$, $L^2$ and the carbon bridge forming a monoanionic ligand bonded to silicon.

2. The Si-containing thin film forming precursor of claim 1, having the following formula:

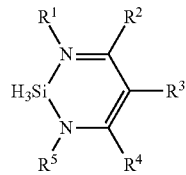

wherein $R^1$, $R^2$, $R^3$, $R^4$, and $R^5$ may each independently be H, a C1 to C6 alkyl group, or a C3-C20 aryl or heterocycle.

3. The Si-containing thin film forming precursor of claim 2, wherein the Si-containing thin film forming precursor is $H_3Si(-(iPr)N—C_3H_3—N(iPr)-)$.

4. The Si-containing thin film forming precursor of claim 1, having the following formula:

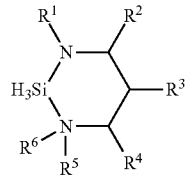

wherein $R^1$, $R^2$, $R^3$, $R^4$, $R^5$, and $R^6$ may each independently be H, a C1 to C6 alkyl group, or a C3-C20 aryl or heterocycle.

5. The Si-containing thin film forming precursor of claim 4, wherein the Si-containing thin film forming precursor is $H_3Si(-(iPr)N—C_3H_6—N(Me)_2-)$.

6. The Si-containing thin film forming precursor of claim 1, having the following formula:

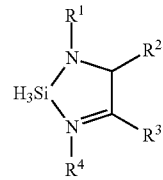

wherein $R^1$, $R^2$, $R^3$, $R^4$, and $R^5$ may each independently be H, a C1 to C6 alkyl group, or a C3-C20 aryl or heterocycle.

7. The Si-containing thin film forming precursor of claim 6, wherein the Si-containing thin film forming precursor is $H_3Si(-(iPr)N—CH_2CH=N(iPr)-)$.

8. The Si-containing thin film forming precursor of claim 1, having the following formula:

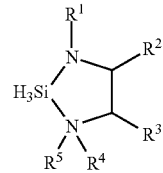

wherein $R^1$, $R^2$, $R^3$, $R^4$, and $R^5$ may each independently be H, a C1 to C6 alkyl group, or a C3-C20 aryl or heterocycle.

9. The Si-containing thin film forming precursor of claim 8, wherein the Si-containing thin film forming precursor is $H_3Si((iPr)NC_2H_4N(Me)_2$.

10. A method of depositing a Si-containing layer on a substrate, the method comprising:
introducing at least one Si-containing thin film forming precursor of claim 1 into a reactor having at least one substrate disposed therein;
depositing at least part of the Si-containing thin film forming precursor onto the at least one substrate to form a Si-containing layer using a vapor deposition method.

11. The method of claim 10, further comprising introducing into the reactor at least one co-reactant.

12. The method of claim 11, wherein the co-reactant is selected from the group consisting of $O_2$, $O_3$, $H_2O$, $H_2O_2$, NO, $NO_2$, a carboxylic acid, radicals thereof, and combinations thereof.

13. The method of claim 11, wherein the co-reactant is selected from the group consisting of $H_2$, $NH_3$, $(SiH_3)_3N$, hydridosilanes, chlorosilanes and chloropolysilanes, alkysilanes, hydrazines, organic amines, pyrazoline, pyridine, B-containing molecules, alkyl metals, radical species thereof, and mixtures thereof.

14. The method of claim 13, wherein the co-reactant is selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof.

15. The method of claim 13, wherein the co-reactant is selected from the group consisting of $SiHCl_3$, $Si_2Cl_6$, $Si_2HCl_5$, $Si_2H_2Cl_4$, and cyclo-$Si_6H_6Cl_6$.

* * * * *